United States Patent [19]
Corlew et al.

[11] Patent Number: 4,789,187
[45] Date of Patent: Dec. 6, 1988

[54] REMOVABLE AND REATTACHABLE INDEX FOR BOUND VOLUMES

[75] Inventors: Robin F. Corlew; Darryl W. Bolduc, both of Charlotte, N.C.

[73] Assignee: Quetzel, Inc., Charlotte, N.C.

[21] Appl. No.: 11,625

[22] Filed: Feb. 6, 1987

[51] Int. Cl.[4] ........................ B42D 1/00; B41L 1/20; B42B 5/00; A61F 13/02

[52] U.S. Cl. ........................ 281/15 R; 282/9 R; 412/33; 428/40

[58] Field of Search ........................ 281/3 R, 15 A, 15 R, 281/22; 282/9 R, 10; 428/40; 412/33; 402/79

[56] References Cited

U.S. PATENT DOCUMENTS

| | | | |
|---|---|---|---|
| 436,983 | 9/1980 | Loewenback | 282/9 R |
| 576,295 | 2/1897 | Watts et al. | |
| 629,214 | 7/1899 | Simpson | |
| 2,123,903 | 7/1938 | Lane et al. | 281/15 R |
| 2,195,646 | 4/1940 | Green | |
| 2,681,655 | 6/1954 | Schade | |
| 2,755,576 | 7/1956 | Golden | 281/15 R |
| 2,797,801 | 7/1957 | Bishop, Jr. | |
| 3,275,316 | 4/1965 | Cleary, Jr. | 281/15 R |
| 3,324,823 | 6/1967 | Peters | |
| 3,350,801 | 11/1967 | Berard | |
| 4,492,306 | 1/1985 | Cooper et al. | 402/79 |
| 4,500,021 | 2/1985 | Bildusas | 428/40 |
| 4,511,298 | 4/1985 | Jones | 412/33 |
| 4,596,407 | 6/1986 | Suska | 281/15 R |
| 4,667,983 | 5/1987 | Spolander | 281/15 R |

FOREIGN PATENT DOCUMENTS

| | | | |
|---|---|---|---|
| 867409 | 5/1961 | United Kingdom | 281/15 R |

*Primary Examiner*—E. R. Kazenske
*Assistant Examiner*—Paul M. Heyrana, Sr.
*Attorney, Agent, or Firm*—Bell, Seltzer, Park & Gibson

[57] ABSTRACT

A removable and reattachable table of contents for bound volumes is disclosed. In a preferred embodiment, the index is the table of contents page of a soft-bound periodical or magazine and is removably attached to the magazine by a series of perforations along one edge. The page additionally carries a releasable self-stick adhesive so that the page can be reinserted and reattached at other desired locations in the volume to provide both a readily available table of contents and a marker at the desired location.

16 Claims, 1 Drawing Sheet

REMOVABLE AND REATTACHABLE INDEX FOR BOUND VOLUMES

FIELD OF THE INVENTION

The present invention relates to the indexing and marking of bound, published materials such as books and magazines.

BACKGROUND

The growth in information and services available to the consuming, business and professional public in recent years had led to a rapid increase in the number and types of publications available for use by consumers, businesspersons, members of the licensed professions, and many others.

One particular area of growth has been in periodical publications, e.g. magazines or journals, which are generally soft bound, carry news of current events or developments, and appear at regular intervals, typically weekly, bi-weekly, or monthly.

Many such periodicals include a relatively large number of entries or articles in each issue. Often for reasons of subject matter or time limitations, persons interested in the subject matter of the periodical as a whole are not interested in every single article or entry.

Given a reader's interest in some, but not all of the articles in such a publication, and given the time limitations involved in reading such materials, as well as the conditions under which they often are read, e.g. during travel periods or other interrupted intervals which arise in business situations, two particular features of using such periodicals become inconvenient to the reader. First, the necessity and difficulty of returning to the table of contents to review which articles are of interest and their respective locations, and second, keeping one's place in the midst of an article or between articles when the reader is interrupted in order to peruse desired articles. A typical periodical reader must either turn through every single page of the periodical or must continually refer to the table of contents, which is often hard to find in a soft-bound periodical, especially one that has been used. For example, once a magazine loses its cover, finding the table of contents among a hundred or more identically appearing pages can be quite difficult. Second, if the reader is interrupted before completing an article of interest, retaining one's place can be difficult, as traditional bookmarks are not as firmly held by soft-bound periodicals as they are by paperback books or hard-bound books.

It is accordingly an object of this invention to provide a table of contents which is particularly suitable for quick and easy reference in periodicals regardless of the condition or previous use of the periodical.

It is another object of this invention to provide a convenient means for marking one's place in such a periodical where the use of a usual type of bookmark is inconvenient, impractical, or even impossible.

It is yet another object of this invention to provide a combination bookmark and table of contents for use with such periodicals in which the table of contents or a reprinted version of it can be positioned and secured in position at any desired page location in the periodical and then can be removed and repositioned at another page location as the reader so desires.

The foregoing and other objects, advantages and features of the invention, and the manner in which the same are accomplished will become more readily apparent upon consideration of the following detail description of the invention taken in conjunction with the accompanying drawings, which illustrate preferred and exemplary embodiments, and wherein.

SUMMARY OF THE INVENTION

The present invention is a bound volume of printed material such as a magazine or periodical with a removable and replaceable index or table of contents which can be positioned and repositioned as desired at any particular page or page location in the bound volume. The invention includes a bound volume having a plurality of individual printed pages which makes up a plurality of indexable printed entries in the bound volume. An indicia page is removeably attached to the bound volume and has an index printed thereon corresponding to the indexable printed entries in the bound volume. The indicia page carries means for removably reattaching the indicia page to any one of the other individual pages of the bound volume, whereby the indicia page may be repeatedly removed from its original position or any other position and reattached to yet any other desired page in the bound volume to thereby mark a desired page or page location for a reader and to also provide a readily available index to the reader at the marked page.

DETAILED DESCRIPTION

Figure 1:
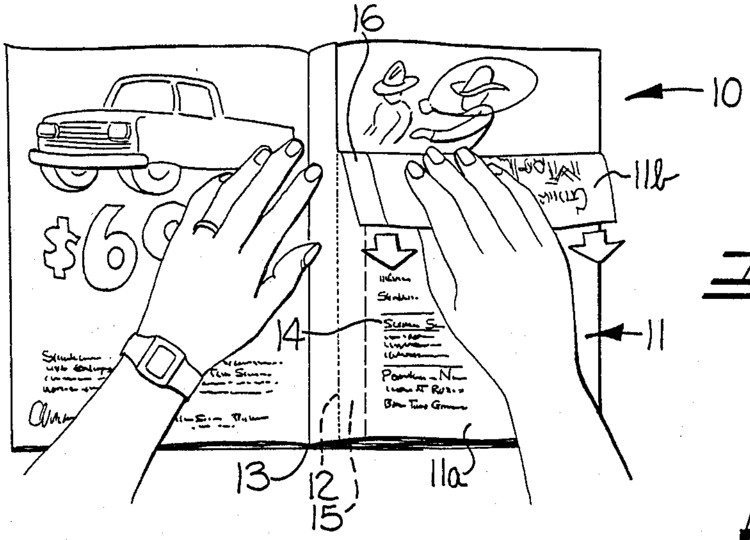
FIG. 1 is a perspective view of a magazine showing a first embodiment of the invention.

FIG. 1 illustrates a first embodiment of the invention. A soft-bound volume such as a staple-bound periodical is broadly designated at 10. An indicia page 11 having front and rear sides **11*a* and 11*b*, respectively, is removably attached to the bound volume 10. In the first embodiment, the indicia page 11 is so attached by a series of perforations 12 which extend along the page 11 parallel to the binding core 13 of the volume 10 and spaced a short distance away therefrom. A series of characters which represent the index or table of contents to the volume are broadly designated at 14. As illustrated in FIG. 1, the table of contents page 11 can be easily removed from the bound volume 10 by pulling the page 11 away from the binding 13 along the perforations 12**.

The table of contents page 11 also carries means for removably reattaching the page to any one of the other individual pages of the bound volume 10. In a preferred embodiment of the invention, a portion of releasable self-stick adhesive designated at 15 is positioned along one edge of the rear side **11*b* of the index page 11. In the illustrated embodiment, the adhesive 15 is positioned adjacent the perforated edge of the page 11**. A number of releasable and reattachable adhesives have become available in recent years. One common use of such an adhesive are the SCOTCH TM brand POST-IT TM notepads which carry an adhesive on a portion of one side which adhesive is characterized in that it provides adhesive properties strong enough to hold one piece of paper to another, but moderate enough so that the papers can easily be removed from one another. It is this type of adhesive which is referred to herein as "releasable self-stick" adhesive, and it will be understood that the commercial example just described is included by way of illustration, and not of limitation.

Figure 2:
FIG. 2 is a view of a rear side of the table of contents page of the embodiment of FIG. 1.

Further to the preferred embodiment, and as illustrated in FIG. 2, the indexed page 11 can also carry a removable protective covering illustrated as the paper backing strip 16. The backing 16 initially covers the releasable self-stick adhesive and avoids the necessity of initially attaching the indexed page in its original location by means of the adhesive so that the page 11 may be initially attached by the relatively more secure binding 13 and by the perforations 12.

Once the indexed page 11 is removed along the perforations 12, however, the paper backing 16 can be removed from the adhesive 15 so that the page 11 may be reinserted and reattached to the desired other page in the magazine.

Figure 3:
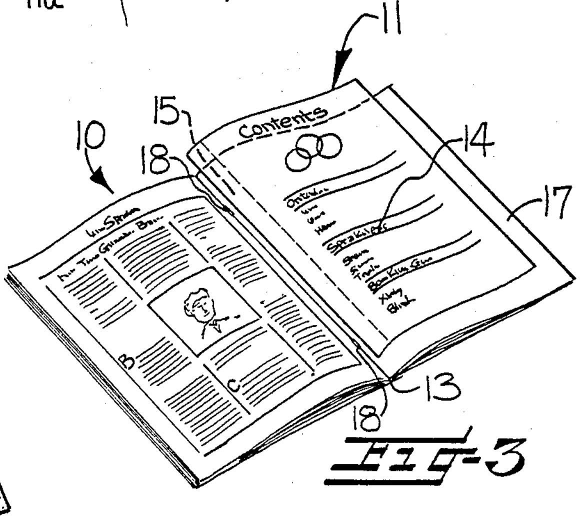
FIG. 3 is a perspective view showing the first embodiment of the invention removably replaced in a new location in a bound volume.

FIG. 3 shows the indexed page 11 attached to an alternative page 17 of a bound volume 10. The characters 14 representing the table of contents are easily visible, and because the page 11 can be offset somewhat from the remainder of the pages, the table of contents page 11 can act as a bookmark as well as a reference page. As indicated by the dotted line parallel to the left-hand border of the page 11, the adhesive 15 on the rear side **11*b* holds the page 11 in place upon the page 17**.

FIG. 3 also illustrates staples 18 for binding the volume 10.

Accordingly, the majority portion of the table of contents page may be initially removed from its original position and temporarily reattached to any other desired page in the bound volume to thereby mark a desired page for the reader and at the same time to provide a readily available index to the reader at the marked page.

Figure 4:
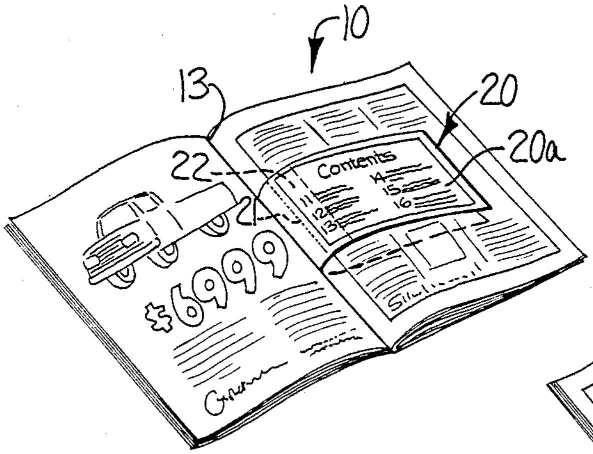
FIG. 4 is a perspective view of a second embodiment of the invention as it would be initially placed in a bound volume by the publisher.
Figure 5:
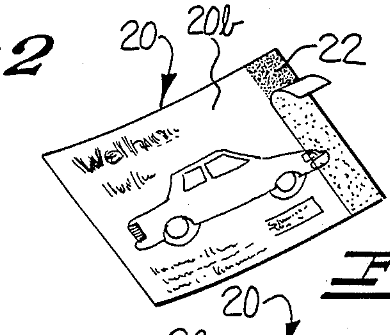
FIG. 5 is a perspective view of the embodiment illustrated in FIG. 4 and showing the rear side thereof.
Figure 6:
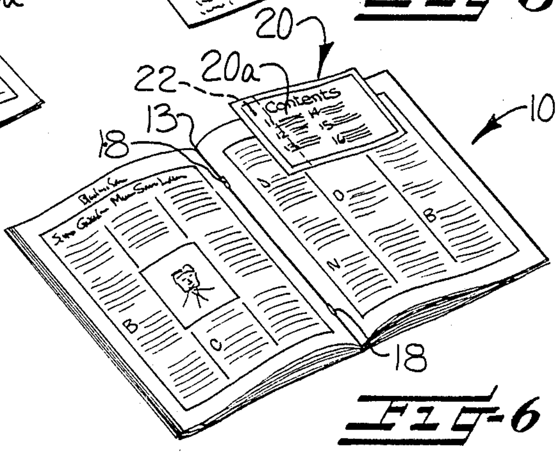
FIG. 6 is yet another perspective view of the embodiment of FIGS. 4 and 5 and showing the table of contents removably reattached to an alternative page in a bound volume.

A second embodiment of the invention is shown in FIGS. 4, 5 and 6. In these figures, the volume is again designated at 10, but the indicia page comprises a smaller, separately attached page such as the card 20 illustrates in FIGS. 4, 5 and 6. Such cards are commonly used as advertising-type inserts in periodicals and are particularly appropriate for use as part of the present invention. The cards are often approximately three inches by five inches in size and may be formed of a paper or cardboard material which is relatively stiffer than the material which makes up the remainder of the pages of the periodical.

As in the first embodiment, the card 20 has a front side **20*a* and a rear side 20*b*. The front side 20*a* carries the index of table of contents, and the rear side 20*b*** can carry advertising or whatever other message the publisher desires or finds appropriate.

As in the previous embodiment, the card is originally fixed along the binding 13 of the volume 10, but includes a series of perforations 21 generally adjacent and parallel to the binding 13 and which form one border of the card 20 when it is removed along the perforations. The non-indexed side of the card similarly carries a removable self-stick adhesive 22, and although not illustrated, can also carry a protective covering such as a paper strip analogous to the strip 16 shown in reference to the first embodiment. FIG. 6 also shows the staples 18.

FIG. 6 shows the second embodiment of the invention in use both as a page marker and as a removable and replaceable table of contents. Although the amount of printed material that can be carried on a card would normally be somewhat smaller than that on a full page, the card embodiment of the invention offers several advantages including potentially easier handling and a stiffer composite structure suitable for being handled numerous times as is the intention of the invention.

In either embodiment, the invention provides a unique and particularly useful method of indexing and using a bound periodical.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A bound volume of printed material such as a magazine or periodical and comprising:

a plurality of individual printed pages bound together at a binding and making up a plurality of indexable printed entries in said bound volume, at least one of said pages having an index printed on at least one of the faces thereof which index is related to said indexable printed entries;

means removably attaching said one page to the others of said pages; and a repeatedly releasable self-stick adhesive carried by said one page on the face of said one page opposite to said at least one face having an index printed thereon for removably reattaching said one page to any one of the other of said pages of said bound volume, whereby said one page may be initially removed from its original position and reattached to another desired page in said bound volume and then repeatedly to another desired page in said bound volume and then repeatedly removed and reattached as desired to thereby mark a page or page location for a reader and to provide a readily available index to the reader at the marked page.

2. A bound volume according to claim 1 wherein said volume comprises a staple-bound volume.

3. A bound volume according to claim 1 wherein said means removably attaching said one page to the others of said pages comprises a series of perforations.

4. A bound volume according to claim 1 wherein said index comprises the table of contents of said bound volume.

5. A bound volume according to claim 1 wherein said releasable adhesive forms a longitudinal strip along one edge of said one page on the face of said one page opposite to said at least one face having an index printed thereon.

6. A bound volume according to claim 1 wherein said indicia page further comprises a removable protective paper backing covering said releasable self-stick adhesive for being removed prior to reattaching said indicia page to another page in said bound volume.

7. A bound volume according to claim 1 wherein said indicia page is formed of a material relatively stiffer than the material making up the remainder of the pages in said bound volume.

8. A bound volume according to claim 1 wherein said indicia page comprises a card approximately three inches by five inches in size.

9. A bound volume according to claim 1 wherein said bound volume comprises a soft-bound periodical and said indicia page comprises the table of contents page of said periodical removably attached to said periodical by a series of perforations positioned adjacent said binding of said periodical.

10. A removable and reattachable index or table of contents page for being bindingly included at an original position in a bound volume such as a magazine or periodical formed of a plurality of printed pages and a binding and having a plurality of indexable printed entries therein, which index page can be removed from its original position and repeatedly repositioned as desired at any particular page in the bound volume, said index page comprising:

means for binding one edge of said page to the binding of a bound volume;

a series of perforations extending adjacent and generally parallel to the said one edge of said page for making at least a portion of said index page removable from a volume to which said page is bound;

a printed index on at least one of the faces of said removable portion of said page, which index corresponds to the indexable printed entries in the volume; and a repeatedly releasable self-stick adhesive carried by said page on the face of the removable portion of said page opposite to said at least one face having an index printed thereon for reattaching said removable portion of said page to any other page in the bound volume whereby said page may be initially removed from its original position and reattached to another desired page in a bound volume and then repeatedly removed and reattached as desired to thereby mark a page or page location for a reader and to provide a readily available index to the reader at the marked page.

11. An index page according to claim 10 wherein said repeatedly releasable self-stick adhesive carried by said index page for removably reattaching said page comprises a longitudinal strip of releasable self-stick adhesive positioned along one edge of said indicia page on the face of said page opposite to said at least one face having an index printed thereon.

12. An index page according to claim 10 further comprising a removable protective paper backing covering said releasable self-stick adhesive for being removed prior to reattaching said index page to another page in a bound volume.

13. An index page according to claim 10 wherein said index page comprises the table of contents page of a periodical within which said index page may be bindingly included.

14. A soft-covered, staple-bound periodical comprising:

a plurality of individual printed pages stapled together to form a binding, said pages making up a plurality of indexable printed entries in the periodical;

an indicia page bound to said binding at an original position in said periodical, said indicia page having a table of contents printed on at least one of the faces thereof which corresponds to the printed entries in said periodical;

a series of perforations on said indicia page extending adjacent and generally parallel to said binding for making at least a portion of said indicia page removable from said periodical; and a longitudinal strip of repeatedly releasable, self-stick adhesive carried by said indicia page adjacent said perforations and on the face of said page opposite said face upon which said table of contents is printed, whereby the indicia page may be removed along said perforations from its original position and be removably reattached to another desired page or page location in said periodical to thereby temporarily mark a desired page or page location for a reader and to provide a readily available index to the reader at the marked page and to allow the reader to reattachably change the position of the card-like table of contents as desired.

15. A periodical according to claim 14 wherein said indicia page further comprises a removable protective paper backing covering said releasable self-stick adhesive for being removed prior to reattaching said indicia page to another page in said periodical.

16. A periodical according to claim 14 wherein said indicia page is relatively smaller in size than the size of the remainder of the pages in said periodical and is formed of a material relatively stiffer than the material making up the remainder of the pages in said periodical.

* * * * *